(12) United States Patent
Webber et al.

(10) Patent No.: US 9,594,087 B2
(45) Date of Patent: Mar. 14, 2017

(54) CASSETTE

(71) Applicant: CellPath Ltd., Powys (GB)

(72) Inventors: Paul Webber, Powys (GB); Philip Webber, Powys (GB); Richard Titcombe, Powys (GB)

(73) Assignee: CellPath Ltd., Powys (GB)

( * ) Notice: Subject to any disclaimer, the term of this patent is extended or adjusted under 35 U.S.C. 154(b) by 0 days.

(21) Appl. No.: 14/493,985

(22) Filed: Sep. 23, 2014

(65) Prior Publication Data

US 2015/0087018 A1    Mar. 26, 2015

(30) Foreign Application Priority Data

Sep. 23, 2013 (GB) .................................. 1316895.0

(51) Int. Cl.
*A61B 10/00* (2006.01)
*G01N 35/00* (2006.01)
*G01N 1/36* (2006.01)

(52) U.S. Cl.
CPC ......... *G01N 35/00732* (2013.01); *G01N 1/36* (2013.01); *G01N 2001/366* (2013.01); *G01N 2035/00801* (2013.01); *G01N 2035/00831* (2013.01)

(58) Field of Classification Search
CPC ...................................................... G01N 1/31
See application file for complete search history.

(56) References Cited

U.S. PATENT DOCUMENTS

| 6,489,171 | B1 | 12/2002 | Aghassi et al. | |
| 7,521,021 | B2 * | 4/2009 | McCormick | G01N 1/31 206/473 |
| 7,927,564 | B2 * | 4/2011 | McCormick | G01N 1/36 422/275 |

FOREIGN PATENT DOCUMENTS

| GB | 1230913 A | 5/1971 |
| JP | H 11132923 A | 5/1999 |
| WO | WO 2009-055603 | 4/2009 |
| WO | WO 2011-041495 | 4/2011 |

OTHER PUBLICATIONS

Extended Search Report from the European Patent Office dated Jan. 19, 2015, for European Application No. 14186033.8-1553.
Search Report dated Mar. 25, 2014 for Application No. GB1316895.0 from the United Kingdom Patent Office.

* cited by examiner

*Primary Examiner* — Jyoti Nagpaul
(74) *Attorney, Agent, or Firm* — Cook Alex Ltd.

(57) ABSTRACT

A histology processing cassette comprising a box comprising a compartment for holding a biological tissue sample, the box having a bottom face comprising at least in part a sample support surface and being transmissible to radiation, an open top face, and two side walls, a back wall and a front wall, the box having dimensions greater than a standard size histology processing cassette and comprising a recess in the front wall adapted to receive a standard size cassette which has a front wall comprising a unique identifier for the biological tissue sample such that upon insertion of the standard cassette in the recess the unique identifier on the front wall of the standard cassette is readable.

10 Claims, 5 Drawing Sheets

CASSETTE

This invention relates to a cassette, in particular a histology processing cassette suitable for processing biological tissue samples and to a method of treating a biological tissue sample, particularly large tissue samples. The invention relates particularly to a large histology processing cassette suitable for processing large biological tissue samples having a recess for receiving a standard size, labelled and/or identified histology processing cassette.

Biological materials for histological examination are processed in large quantities for a wide range of diagnostic purposes. Tissue samples are prepared typically by a process involving embedding the tissue sample in paraffin wax and slicing the embedded sample very thinly using a microtome. Prior to embedding the sample, it is treated using solutions selected according to the nature of the sample. The sample is suitably fixed, dehydrated, cleared, infiltrated with molten paraffin wax and optionally stained. Typical fluids employed in such processing may include ethanol, xylene, formaldehyde and water. Processing in which the sample is contacted with a processing solution and contacted with paraffin wax typically involves cooling and may take place over an extended period, for example overnight. Typically, a large number of samples, for example around 50 are processed together.

Embedding the tissue in paraffin wax provides it with the rigidity necessary for further processing, for example microtome slicing. The processing usually involves placing the material in a small box-like plastics carrier, known in the art as a "cassette".

Known cassettes for processing biological tissues typically comprise an open-topped box with a perforated bottom wall. The box may have a perforated top cover which is moveable relative to the box or a removable perforated cover. The cassette typically has a three vertical side walls and the fourth, side wall, on the front side of the cassette is typically sloping and includes an area for labelling and/or identifying the cassette. The perforations of the box and cover are typically from 1 to 3 mm in diameter. Known processing cassettes are described in GB 1230913 and U.S. Pat. No. 3,674,396. Such processing cassettes are used with the cover in place as a tissue processing capsule and with the cover removed for embedding a specimen in paraffin. The processing cassette defines a cavity, which may be closed with the use of a perforated lid, into which the biological tissue is placed for processing. Generally, processing cassettes define one cavity and process one sample at a time although cassettes having multiple cavities to allow processing of more than one sample are known. Processing cassettes are typically constructed of plastics material and the perforations are made in the plastics material which forms the bottom wall and, where employed, the plastics material forming the lid.

The cassette is generally of a "standard size" as it is required to fit in other apparatus, for example fit standard specimen holders, known as chucks, of microtomes. "standard size" histology processing cassettes typically have internal dimensions of 28 to 32 mm×25 to 28 mm×5 to 6 mm, typically a maximum size of 30 to 31 mm by 25 to 26 mm. Minor variations in size may occur, dependent for example upon the wall thickness of the box.

In processing biological tissue samples, it is essential that the cassette be marked with a unique identifier so as to provide unique identification of the source of the sample, for example a patient. Standard size cassettes are typically automatically marked using a machine which imparts a unique identifier, for example a 2-dimensional bar-code, on the sloping front side wall. The marking suitably is indelibly applied to the cassette for example by printing onto or etching into the material from which the cassette is constructed.

Large numbers of cassettes, for example 30 to 50 may be processed simultaneously and automated labelling enables rapid throughput and with the unique identification data being stored electronically offers a failsafe system of ensuring the identifier on the cassette corresponds to the sample being processed in the cassette. Devices for electronically applying a unique identifier to cassettes are known and are tailored to receive cassettes of the standard size and represent a significant capital investment. The unique identifier is typically taken from electronically stored patient records, for example from a Laboratory Information Management System so that patient data need be input in the system only once, errors in manual labelling or transcription are avoided Whilst standard size cassettes may be employed for the majority of tissue samples, certain samples, for example prostate samples are larger than the standard size cassette and require a larger cassette. Larger cassettes typically have an area four times that of a standard cassette and a depth of around twice that of a standard cassette, for example dimensions of around 50 to 55 by 65 or 70 to 75 or 80 by 12 to 17 mm are conventionally employed for use in processing larger samples. The ratio of the length, to the width and to the depth of a larger cassette is therefore approximately the same as that of a standard sized cassette.

In known larger cassettes, samples may curl or otherwise move prior to or during processing within the volume of the cassette, due to the depth being 12 to 17 mm. This may be problematic from a processing viewpoint and also in ensuring the sample is appropriately oriented for subsequent processing, for example sectioning and microscopy.

Known devices for applying the unique identifier to histology processing cassettes are not adapted to receive larger size cassettes and conventionally, the patient information is applied to the larger cassette manually, for example by writing the unique identifier on the cassette or by some other manual method in order to identify the cassette. This method of labelling the sample is unsatisfactory in that it relies on accurate manual reproduction of critical data and the applied information may smudge or be removed during processing of the sample. Manual application is also inefficient, especially given that large numbers of samples may be processed simultaneously.

During processing, the sample in the cassette is typically subjected to a long processing cycle, for example overnight, and is contacted with processing fluids, for example xylene, alcohol and the like. This processing runs the risk that the unique identifier will be lost or otherwise rendered useless in identifying the sample with the patient and large numbers of samples may need to be re-processed.

Furthermore, investment in further devices for applying a unique identifier to a larger cassette in addition to devices for applying unique identifiers to standard size cassettes represents a considerable investment.

We have now devised a larger sized histology processing cassette which ameliorates the disadvantages of employing manual techniques without the need to invest in costly marking devices or apparatus adapted to receive larger sized histology processing cassettes.

The invention provides in a first aspect a histology processing cassette comprising a box comprising a compartment for holding a biological tissue sample, the box having a bottom face comprising at least in part a sample support surface and being transmissible to radiation or a flow of fluid through the face, an open top face, and two side walls, a back wall and a front wall, the box having dimensions greater than a standard size histology processing cassette and comprising a recess in the front wall adapted to receive a standard size cassette which has a front wall comprising a unique identifier for the biological tissue sample such that upon insertion of the standard cassette in the recess the unique identifier on the front wall of the standard cassette is readable.

The term "transmissible" as employed herein means that radiation or fluid for processing or analysis is able to pass through apertures or perforations in the face whether a plastics face with apertures or perforations or a gauze.

In a second aspect, the invention provides a histology processing assembly comprising a histology processing cassette according to the first aspect of the invention in combination with a standard size histology processing cassette which standard size cassette comprises a bottom face and two side walls, a back wall and a front wall, the front wall comprising a unique identifier such that upon insertion of the standard cassette in the recess the unique identifier on the front wall of the standard cassette is readable.

The invention also provides for a histology processing apparatus comprising, in combination, apparatus for processing or analysing a biological sample and a histology processing assembly according to the first or second aspect of the invention.

The invention further provides for use of a histology cassette according to the first aspect of the invention or a histology processing assembly according to the second aspect of the invention in the preparation of a sample for analysis or for analysis of a sample for example by irradiation or by flow of fluid through the face for processing or analysis.

The invention also provides a method of uniquely identifying a biological sample in a larger size histology cassette comprising:
  i) providing a histology processing cassette according to the first aspect of the invention and the cassette being adapted to be received in apparatus for processing a biological sample;
  ii) applying a unique identifier for the biological sample to a standard size histology cassette;
  iii) loading the standard size cassette into the recess in the histology processing cassette such that the unique identifier on the standard size cassette, preferably the front wall of the cassette, is readable;
  iv) loading a biological sample into a sample compartment in the said histology processing cassette whereby the biological sample may be uniquely identified from the unique identifier on the standard size cassette;
  v) optionally inserting the histology processing cassette into apparatus for analysing or processing a biological sample; and
  vi) optionally carrying out analysis or processing of the sample to provide analytical results from the sample.

Advantageously, the invention enables samples to be processed in larger sized cassettes with the cassette being clearly labelled with a unique identifier to ensure the identity of the sample remains known and traceable throughout processing or analysis. The unique identifier may be applied to the standard size cassette in any known manner, for example manually or preferably automatically to reduce the risk of errors of transcription.

In a preferred embodiment, the unique identifier is applied to the standard sized cassette by printing from a standard laboratory printer, typically employed in a laboratory.

Preferably the unique identifier is generated by a record management system and applied automatically. The invention enables a larger cassette to have a unique sample identifier affixed to it but allows existing apparatus used to mark a standard sized cassette to be employed without the need to invest in apparatus adapted to mark a larger cassette with the unique identifier.

The unique identifier may be in any form provided it unambiguously allows identification of the sample and the source of the sample, typically a human or animal. The unique identifier may be linked to an information record for example in a patient record system or may itself contain information. The unique identifier may be embossment but is desirably two dimensional. Preferably, the identifier is indelibly marked on the cassette and remains legible or readable throughout the processing or analysis. The unique identifier may comprise alpha-numeric representation or another form of representation, for example a bar code. In an especially preferred embodiment, the unique identifier is allocated by a data system containing the records of the source from which the sample is derived and, as desired, other information as may be required.

Suitably the samples being analysed comprise biological tissue samples. The histology processing cassette suitably has an area of two to six times, preferably four times that of a standard cassette and an external depth of around two to three times that of a standard cassette, for example dimensions of around 50 to 55 by 65 or 70 to 75 or 80 by 12 to 17 mm and is adapted to engage with a cassette-receiving site in apparatus for histological examination, processing or analysis of a larger biological tissue sample than is analysed in a standard size cassette.

The compartment for holding the tissue samples is suitably located in an upper portion of the box and the recess is located in a lower portion of the box and under the sample support surface. Suitably the recess is located within the thickness of the bottom face of the cassette.

The compartment located in the upper portion of the box preferably has dimensions of 50 to 55 mm by 65 or 70 to 75 or 80 mm and a depth of 5 to 10 mm, for example 8 or 9 mm. The bottom face of the cassette preferably has dimensions of 50 to 55 mm by 70 to 80 mm and a depth of 2 to 12 mm, preferably 5 to 10 mm, for example 7 to 8 mm. As the depth of the sample compartment in the cassette is significantly shallower than sample compartments in known larger size cassette, the sample is less able to curl or otherwise move within the compartment as well as a more consistent thickness to be processed and drawbacks associated with this are therefore ameliorated.

The bottom face of the cassette suitably has a thickness which is at least as great as the external depth of a standard sized cassette whereby the standard sized cassette may be accommodated within the thickness of the bottom face of the larger cassette. The internal side of the bottom face of the cassette may be located around half way up the side walls of the cassette such that the depth of the cassette when viewed from the side of the cassette comprises an upper portion which defines the sample compartment and a lower portion within which the recess for receiving the standard cassette is located.

Suitably, the standard cassette fits snugly within the recess so as to minimise relative movement of the standard sized cassette relative to the larger cassette during processing. The standard sized cassette and the recess may comprise complementary inter-engaging means such that the standard sized cassette is locked into the recess upon insertion.

Preferably, the front wall of the standard sized cassette carries the unique identifier for the sample and is readily visible and accessible for automated reading by equipment such as barcode readers when the standard sized cassette is located in the recess. Preferably, the front wall of the larger cassette comprises the front wall of the standard sized cassette upon insertion.

The compartment for holding biological tissue extends between the top face and the bottom face of the cassette to define one or more compartments for receiving the sample or samples to be analysed. The bottom of the sample compartment and the top of it where employed are suitably transmissible to X-ray or other radiation. The bottom of the cassette and, where present, the top or lid suitably comprises perforations in a plastics face or a mesh, for example a polyamide mesh.

The box may comprise a single compartment or multiple compartments. Preferably, the compartment is at least 5 mm wide in their smallest dimension parallel to the top or bottom face. Where multiple compartments are employed, the compartments may be any suitable shape, for example elongate and square and may be arranged in any desired manner in the cassette. Preferably, the compartments are arranged to extend across the full width of the cassette. Endoscopy biopsies for example, may be processed in compartments which are more square than elongate.

Suitably, the top face of the histology processing cassette is covered by a lid comprising a plastics sheet having perforations and engages releasably with the box of the cassette. Suitably, the lid is moveable relative to the box of the histology processing cassette. Preferably the lid is detachable and the lid and box have complementary engaging means, for example, recesses and lugs, to allow secure attachment of the lid to the box. If desired, the lid may be permanently attached to the box and pivotally mounted, for example through a hinge, to the box.

The lid of the box is suitably pivotally mounted on the box and adapted in a first configuration to be open wherein the lid is at an angle to the box of less than 170 degrees, preferably 100 to 140 degrees, and in a second configuration to close the compartment.

Preferably the cassette is constructed of a plastics material as is the lid where applicable. Suitably these parts are constructed by injection moulding a thermoplastics material.

The apparatus for processing or analysing a biological sample may be semi-automatic or automatic. Examples of suitable apparatus include section cutting equipment, embedding equipment, X-ray apparatus and any other histopathology apparatus.

Suitably, the cassette or adaptor according to the invention is substantially transparent to X-rays or other radiation frequencies as desired to allow it to be employed in the examination of samples which are to be examined by irradiation.

The histology processing cassette and assembly of the present invention provide practical advantage in preparation of a specimen for analysis.

In a further aspect the invention provides a method of preparation of a biological sample for analysis comprising:
i) allocating a unique identifier to a biological sample;
ii) applying the unique identifier to a standard size cassette;
iii) inserting the standard size cassette into a histology processing cassette according to the first aspect of the invention and locating the biological sample in the histology processing cassette optionally;
iv) treating the biological sample by contacting the biological sample with an organic material including molten wax;
v) removing the biological sample from the histology processing cassette and placing the sample in a mould adapted to engage with the histology processing, preferably the bottom face of the histology processing cassette, and engaging the cassette with the mould to form a mould assembly;
vi) adding molten wax to the mould assembly to fill the mould and at least partially, and preferably completely, filling the compartment of the histology processing cassette with molten wax;
vii) solidifying the molten wax or allowing the molten wax to solidify so as to provide a wax block containing the biological sample and its unique identifier ready for analysis for example by sectioning in a microtome.

Suitably the tissue samples are fixed in a conventional manner, for example using formalin. The sample or specimen is then given a unique identifier which may include a work reference number by a data or records management system. The unique identifier is then applied to a standard size cassette and the cassette inserted into a histology processing cassette according to the first aspect of the invention. The sample is suitably prepared and inserted into the histology processing cassette and, where used, the lid of the cassette is closed. The sample is then processed, for example by passing one or more organic materials through the sample to remove components of the specimen, for example water and fat, and passing a wax, for example paraffin wax through the sample in preparation for slicing and histological study. The sample or specimen is then suitably placed in a wax mould in an orientation suitable for analysis and encased in molten wax. The mould may comprise a receptacle, suitably of the same shape and dimensions as the cassette whereby the receptacle and cassette fit snugly. The histology processing cassette is suitably then placed on the surface of molten wax in the mould and further wax is added through the cassette. The mould containing the sample and wax together with the cassette is then left to solidify, for example on a cold plate, thereby to encase the sample or specimen.

The sample remains uniquely identifiable during the preparation process and through subsequent analysis. The cassette and also acts as a support structure for mounting the wax block for further processing or analysis, for example in a microtome for sectioning. After sectioning, the wax/specimen section may then be analysed, for example by microscopy.

The sample compartment of the histology processing cassette according to the invention has a shallower depth than the sample compartment of conventional larger size cassettes, typically 15 mm deep, and the volume of molten wax required in forming the block assembly is less. Advantageously, the molten wax takes a shorter time to set than for a conventional larger cassette, for example 20 to 40 minutes rather than 1 hour. This enables a higher throughput of mounting blocks for a given volume in a cooler.

Furthermore, the volume of solid wax in the block assembly may be ⅓ to ½ of that in a conventional size wax block and less trimming and therefore shorter processing time, of the mounting block is required.

The mounting block comprises a solid wax part in the mould and a solid wax part in the compartment of the cassette, the two parts being bonded through apertures or perforations in the sample support surface of the cassette. For a given size support surface, a higher proportion of aperture or perforation area advantageously allows thicker wax bonds between the two parts, providing stronger structural integrity.

The present invention is further described by way of example only with reference to the accompanying drawings, in which.

Figure 1:
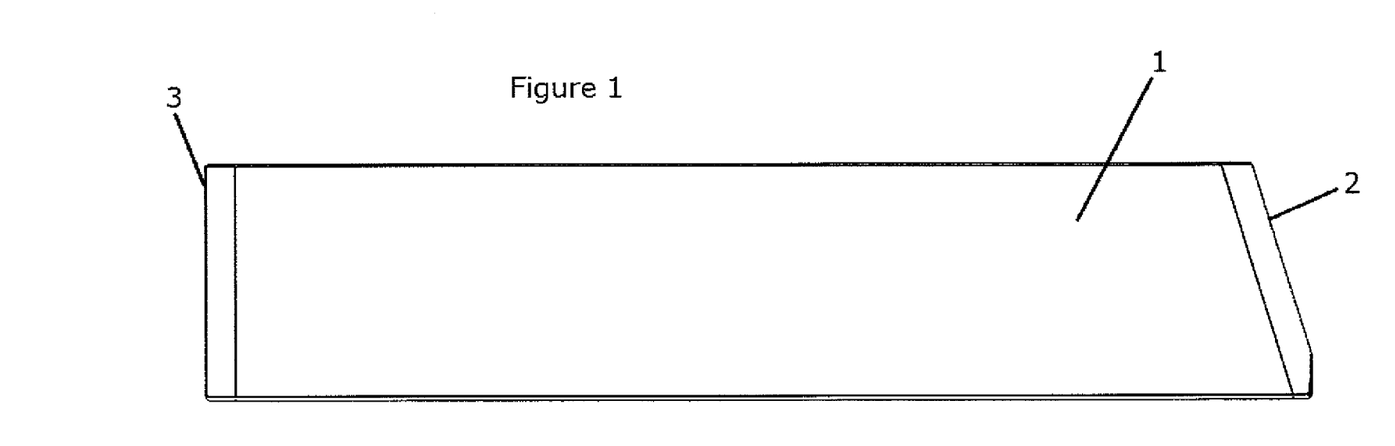
FIG. 1 shows a side elevation of a larger sized known histology processing cassette.

FIG. 1 shows a known histology processing cassette 1 having a front wall 2 and a back wall 3. The cassette has an external length of 75 mm and a depth of 16 mm.

Figure 2:
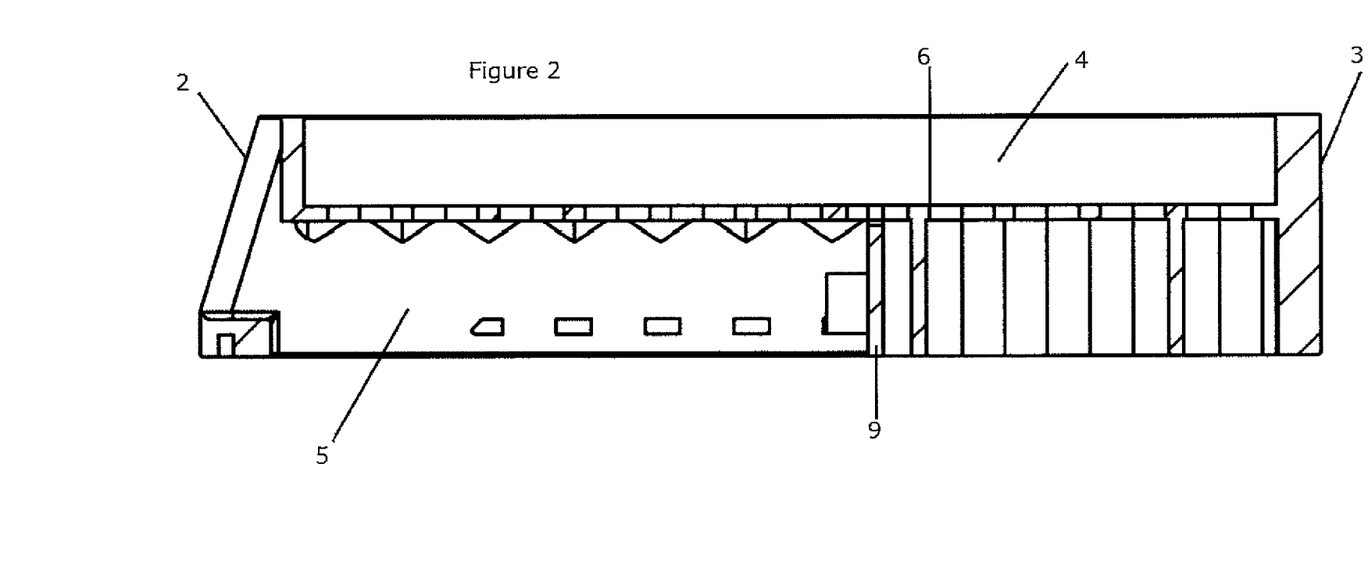
FIG. 2 shows a side section of a larger sized histology processing cassette without a lid according to the invention.
Figure 6:
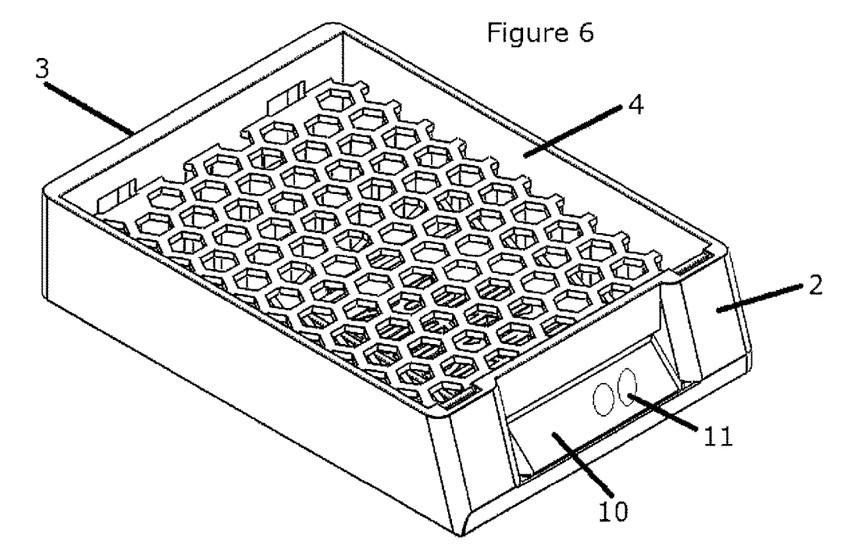
FIG. 6 shows a perspective view of a larger sized histology processing assembly according to the invention comprising a larger sized histology processing cassette with a standard sized histology processing cassette having a unique identifier inserted into the recess.
Figure 7:
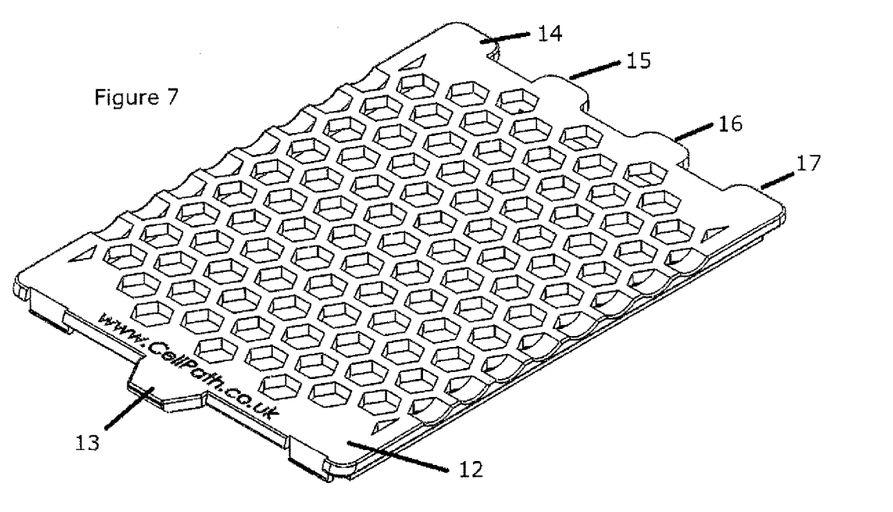
FIG. 7 shows a perspective view of a lid for a larger sized histology processing cassette according to the invention.

FIG. 2 shows a histology processing cassette according to the invention having a sloping front wall 2 and vertical back wall 3. The sample to be processed is locatable in compartment 4. The cassette has a recess 5 which has dimensions the same or slightly greater than the external dimensions of a standard sized histology processing cassette. The depth of the recess is 6 mm at the entrance to the recess in the front wall 2. The standard sized cassette may be inserted into the recess 5 via an opening in front wall 2. The bottom face of the cassette has an upper surface 6 upon which the sample is placed. The upper surface 6 of the bottom face is located at a level such that the sample compartment 4 is above the recess 5. The bottom face 6 has perforations which may be of any shape but, as illustrated in FIGS. 3 to 7, are hexagonal. The external dimensions of the cassette are the same as the external dimensions of the known cassette in FIG. 1. The cassette 1 may be employed with or without a lid 12 as shown in FIG. 7 as desired.

Figure 3:
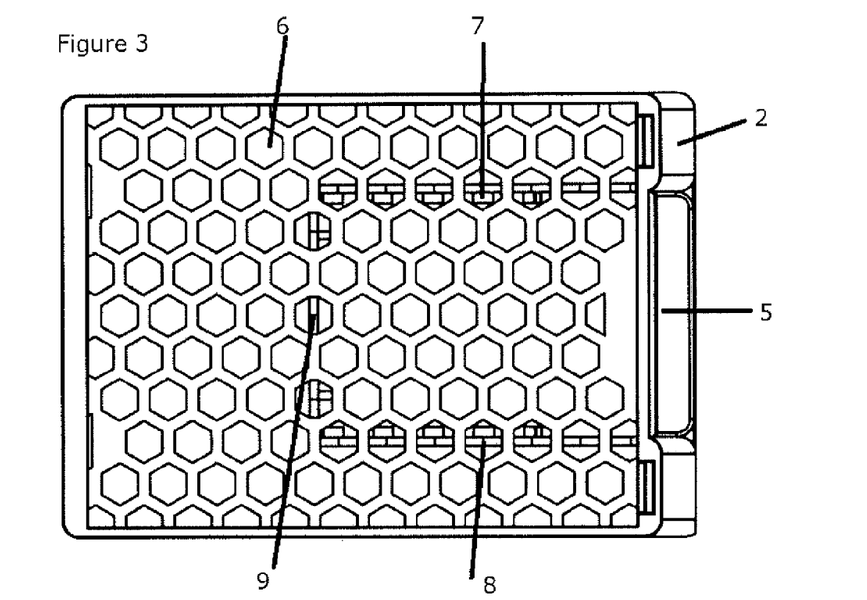
FIG. 3 shows a plan view of a larger sized histology processing cassette without a lid according to the invention.

In FIG. 3, walls 7 and 8 are shown and define the recess 5. Wall 9 forms the back wall of the recess 5. The standard sized cassette having a unique identifier for the sample is inserted into the recess 5 via an aperture in the front wall 2.

Figure 4:
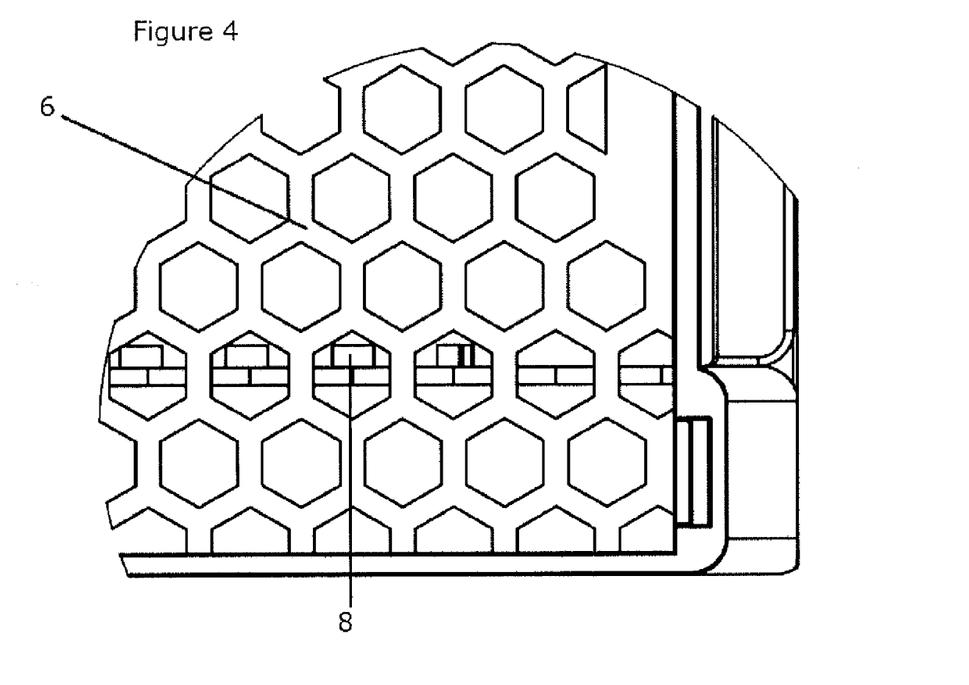
FIG. 4 shows a plan view of a part of the larger sized histology processing cassette shown in FIG. 3.

FIG. 4 a part of the cassette shown in FIG. 3. Indicating preferred dimensions for perforations in upper surface 6.

Figure 5:
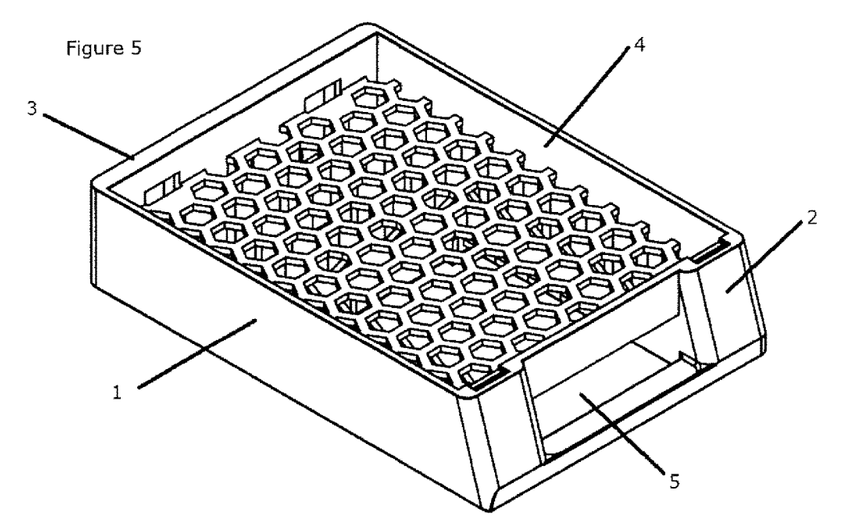
FIG. 5 shows a perspective view of a larger sized histology processing cassette without a lid according to the invention.

FIG. 5 shows a histology processing cassette 1 dimensioned and shaped to be loadable in and removable from apparatus for processing biological samples. The cassette has side walls and a back wall 3 and front wall 2 which with the upper surface 6 of the base face define the sample compartment 4. The standard sized cassette is not inserted in recess 5. In FIG. 6, the standard sized cassette is inserted in the recess 5 via an aperture in front wall 2. The front wall 10 of the standard sized cassette is visible and contains unique identifier 11. The unique identifier 11 has been applied to the standard sized cassette using a conventional device for applying a unique identifier to a standard sized cassette. Upon insertion of the standard sized cassette in the recess 5, the larger sized cassette 1 is labelled with the unique identifier which has been applied automatically using electronically stored data without the need to incur costs for a device for marking a larger sized cassette.

FIG. 7 shows a detachable lid 12 for the larger sized cassette having interengaging means 13-17 for engaging with the cassette 1 and for opening the lid.

Figure 8:
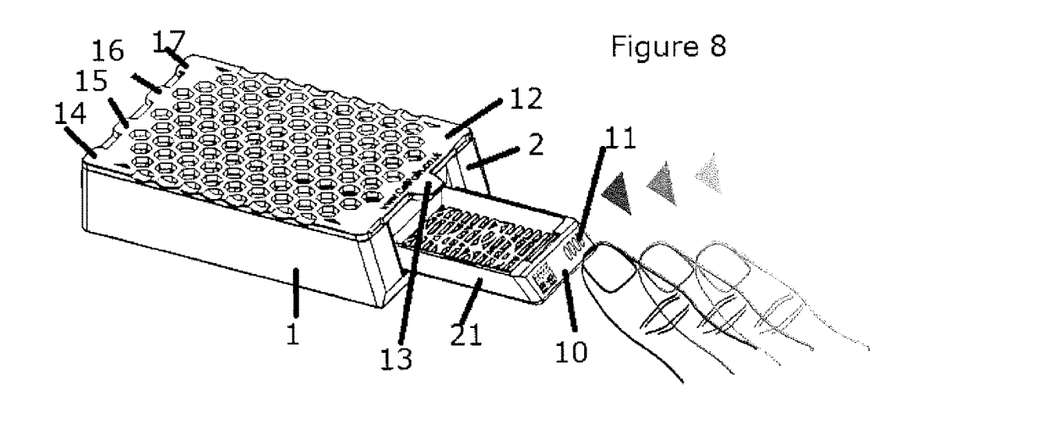
FIG. 8 shows a perspective view of a larger sized histology processing cassette with a lid according to the invention with a standard sized histology processing cassette being inserted into the larger cassette.

FIG. 8 shows a standard size cassette 21 with a unique identifier 11 on its front wall 10 which may be applied for example by printing in a laboratory printer linked to a data records system, being inserted into recess 5 of a larger histology processing cassette 1 having a lid 12 with a sample in the compartment 4 of the cassette 1. The compartment 4 is dimensioned such that it has a length and width approximately the same as the cassette but the compartment 4 is located above the recess 5 and has a depth of 7 or 8 mm, approximately half of the depth of the cassette 1.

Figure 9:
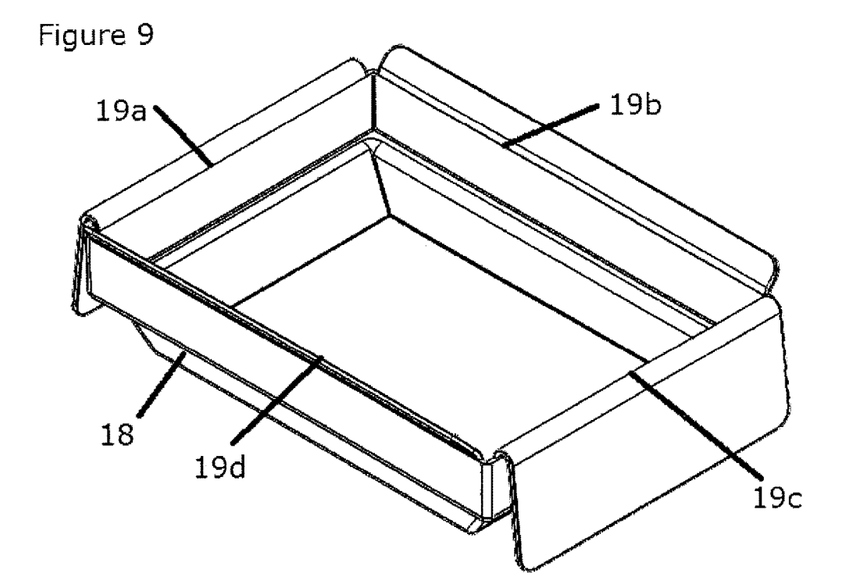
FIG. 9 shows a perspective view of a mould adapted to engage with a histology processing assembly according to the invention.

FIG. 9 shows a mould 18. The histology processing cassette 1 is dimensioned such that it may sit snugly on the periphery of the mould defined by walls 19a to 19d. Molten paraffin wax is then passed through the perforations in the lid 12, through the sample in the compartment 4 and through the sample support surface 6 on the bottom face. The sample is placed in the mould 18, the cassette is placed on top of the mould 18, engaging with the periphery thereof and molten paraffin wax is passed through the cassette 1 into the mould 18. The wax is then allowed to solidify whereby the cassette 1 with its unique identifier 11 is bound to the sample in a mould assembly.

Figure 10:
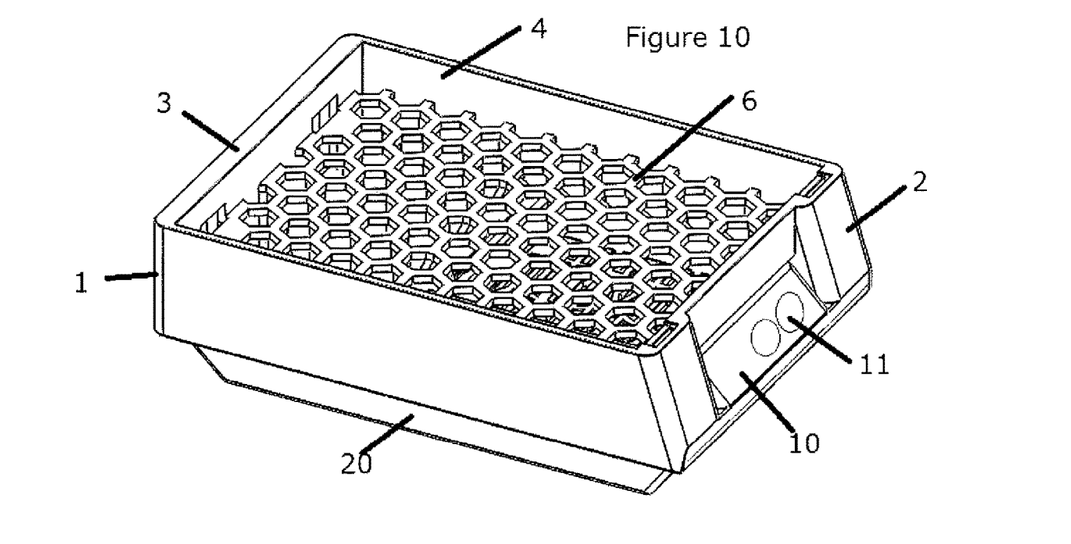
FIG. 10 shows a perspective view of a mould assembly comprising a histology processing assembly according to the invention with a solidified paraffin wax block.

Mould assembly is shown in FIG. 10 and comprises a cassette 1 bound to a wax block 20 in which the sample is embedded and ready for subsequent processing or analysis with the unique identifier 11 being visible.

The invention is claimed as follows:

1. A histology processing cassette comprising a box comprising a compartment for holding a biological tissue sample, the box having a bottom face comprising at least in part a sample support surface and being transmissible to radiation, an open top face, and two side walls, a back wall and a front wall, the box comprising a recess in the front wall adapted to receive a standard size cassette and the box having dimensions greater than a standard size histology processing cassette such that the box is adapted to envelop the standard cassette wherein the standard cassette has a front wall comprising a unique identifier for the biological tissue sample wherein the compartment is located in an upper portion of the box and the recess is located in a lower portion of the box and under the sample support surface the arrangement being such that upon insertion of the standard cassette in the recess the unique identifier on the front wall of the standard cassette is readable.

2. A cassette according to claim 1 comprising a lid transmissible to radiation for closing the open top face of the cassette.

3. A cassette according to claim 2 in which the lid is moveable relative to the box of the cassette and is detachable.

4. A cassette according to claim 2 in which the lid is moveable relative to and permanently attached to the box.

5. A cassette according to claim 4 in which the lid is pivotally mounted on the box.

6. A cassette according to claim 5 wherein the compartment located in the upper portion of the box has dimensions of 50 to 55 mm by 65 to 80 mm by 5 to 10 mm.

7. Histology processing apparatus comprising, in combination, apparatus for processing or analysing a biological sample and a histology processing assembly according to claim 6.

8. A cassette according to claim 1 in which the box comprises a plurality of compartments defined by at least one partition wall which is generally perpendicular to the bottom face and top face.

9. A histology processing assembly comprising a histology processing cassette according to claim 1 in combination with a standard size histology processing cassette which standard size cassette comprises a bottom face and two side walls, a back wall and a front wall, the front wall comprising a unique identifier such that upon insertion of the standard cassette in the recess the unique identifier on the front wall of the standard cassette is readable.

10. A method of uniquely identifying a biological sample in a larger size histology cassette comprising:
   i) providing a histology processing cassette according to claim 1 and the cassette being adapted to be received in apparatus for processing a biological sample;
   ii) applying a unique identifier for the biological sample to a standard size histology cassette;
   iii) loading the standard size cassette into the recess in the histology processing cassette such that the unique identifier on the standard size cassette, preferably the front wall of the cassette, is readable;
   iv) loading a biological sample into a sample compartment in the said histology processing cassette whereby the biological sample may be uniquely identified from the unique identifier on the standard size cassette;
   v) optionally inserting the histology processing cassette into apparatus for analysing or processing a biological sample; and
   vi) optionally carrying out analysis or processing of the sample to provide analytical results from the sample.

* * * * *